United States Patent [19]

Schaefer

[11] 3,959,732
[45] May 25, 1976

[54] SIGNAL PROCESSING SYSTEM AND METHOD

[75] Inventor: Louis F. Schaefer, Palo Alto, Calif.

[73] Assignee: Stanford Research Institute, Menlo Park, Calif.

[22] Filed: July 22, 1974

[21] Appl. No.: 491,158

[52] U.S. Cl. ............................ 328/151; 307/235 C; 328/145
[51] Int. Cl.² ...................... H03K 9/02; H03K 1/14
[58] Field of Search .................... 328/150, 151, 145; 330/86, 110; 307/235, 230

[56] References Cited
UNITED STATES PATENTS

| | | |
|---|---|---|
| 3,108,197 | 10/1963 | Levin .............................. 328/145 X |
| 3,659,082 | 4/1972 | Rolfe ............................. 328/145 X |
| 3,701,909 | 10/1972 | Holmes et al. .................. 328/151 X |

OTHER PUBLICATIONS

C. R. Hoffman, "Eye Opening Detector," Nov. 1970, pp. 1499–1500, IBM Technical Disclosure Bulletin, Vol. 13, No. 6.

B. Bjorkman et al., "Peak Picking and Noise Suppression Circuitry," Nov. 1966, IBM Technical Disclosure Bulletin, Vol. 9, No. 6, pp. 588–589.

Primary Examiner—John Zazworsky
Attorney, Agent, or Firm—Victor R. Beckman

[57] ABSTRACT

A receiver signal processing system and method are shown which are representative of a plurality of signal channels for processing a plurality of electrical signals produced, for example, by an array of transducer elements. The system includes amplifier means which is supplied with an a-c input signal such as the output from an acoustic transducer element included in an array thereof. The output of the amplifier means is connected to a signal level detector, and the detector output is coupled to signal storage means through receiver signal gating means. The signal storage means simply may comprise a capacitor which functions as an analog peak signal detector and storage means such that the peak signal from the signal level detector is stored therein when a receiver gating pulse is supplied to the receiver gating means to enable the same. At the end of the receiver gating pulse the signal storage means is disconnected from the signal level detector and thereby rendered insensitive to changes in output therefrom. The power supply to all of the receiver signal channel amplifiers is switched off during this time to reduce heat generation and problems associated therewith. The output from the signal storage means subsequently is passed through a readout gating means to a utilization circuit, such as a cathode ray tube.

13 Claims, 4 Drawing Figures

SIGNAL PROCESSING SYSTEM AND METHOD

ORIGIN OF INVENTION

The invention described herein was made in the course of work under a grant or award from the Department of Health, Education and Welfare.

BACKGROUND OF INVENTION

There are a number of arrangements wherein a plurality of simultaneously produced electrical signals must be amplified, possibly stored and subsequently converted into useful video information which can be recorded, displayed or otherwise utilized. For example, acoustically operated imaging, testing and like systems may include an array of receiving transducer elements for converting acoustic energy impinging thereon to electrical signals. The transducer signals are supplied to a receiver having a plurality of signal processing channels for amplification, storage and gating thereof to produce the useful video signal. For operation over an extended range of input signals the amplifier means may be switched from linear to logarithmic mode. One such arrangement is shown in copending U.S. patent application Ser. No. 411,729, filed Nov. 1, 1973, the subject matter of which application is specifically incorporated herein by reference.

SUMMARY OF INVENTION AND OBJECTS

An object of this invention is the provision of an improved sequentially operated system and method of signal amplification, detection and storage means which is well adapted for use in a receiver employing a plurality of such systems.

An object of this invention is the provision of a system and method of the above-mentioned type in which amplifier power may be switched off during signal storage without disturbing the level of signal stored.

An object of this invention is the provision of amplifier means which simply may be switched for operation in either a linear or logarithmic mode.

An object of this invention is the provision of a linear/logarithmic amplifier means of the above-mentioned type which may be switched between said operating modes with a minimum change in amplifier gain at zero level input signal.

The above and other objects and advantages are achieved by use of an amplifier means having an output applied to a signal level detector. Receiver signal gating means, when enabled, connects the output from the signal level detector to a signal storage means where the peak signal from the detector is stored for subsequent use. Power to the amplifier means then may be removed until after the stored signal is read out and another signal is to be amplified and stored. The stored signal is supplied through readout gating means to any suitable utilization circuit. If the stored signal is not erased during readout, a discharge gate signal is supplied to the readout gating means and to discharge gating means connected thereto through which the signal storage means is discharged. The amplifier means has a db voltage gain characteristic which varies substantially linearly with changes in gain control potential. Amplifier operation is changed from a linear to a logarithmic mode of operation, when desired, simply by switching the output from the signal level detector to the gain control terminal thereof. To avoid change in the amplifier gain under zero level input signal conditions when switching between the linear and logarithmic operating modes, a d-c bias potential is supplied to the signal level detector which substantially equals the nominal gain control potential.

DESCRIPTION OF PREFERRED EMBODIMENT

Figure 1:
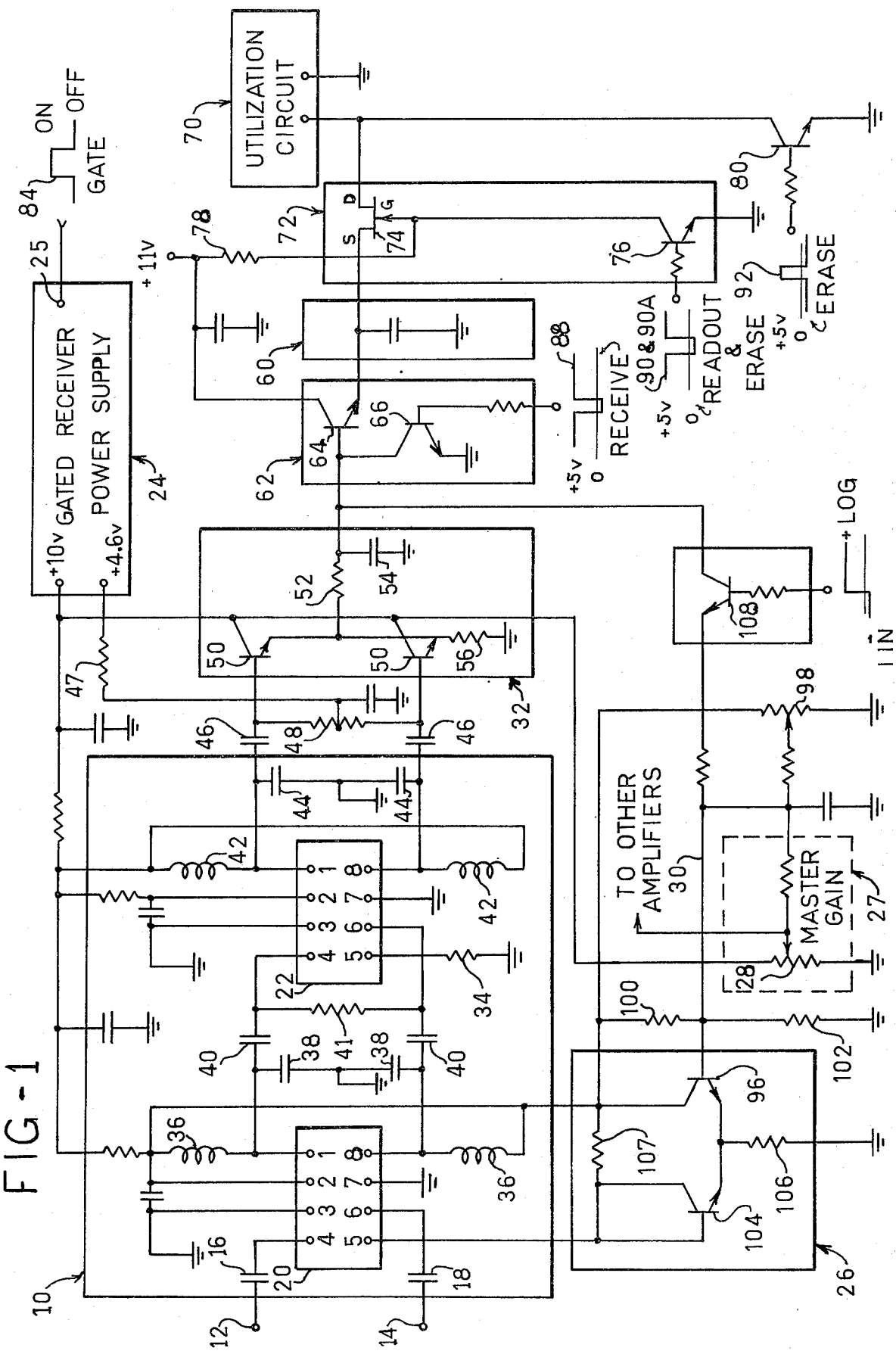
FIG. 1 is a combination block and schematic circuit diagram of a signal amplifying, detecting and storage system embodying this invention.

Reference is made to FIG. 1 wherein there is shown amplifier means 10 to which an a-c input signal is supplied via terminals 12 and 14. The illustrated amplifier means is of the balanced, or differential, input and balanced, or push-pull, output type. As will become apparent, certain single ended amplifier means and combination single and double ended amplifier means may be used, it being understood that the invention is not limited to the particular balanced amplifier input and output arrangements shown.

As mentioned in BACKGROUND OF INVENTION above, the illustrated signal processing system may be employed in one channel of a multichannel arrangement which includes a plurality of similar signal processing systems, such as an acoustic camera. In such a case, the input signal may comprise an amplitude modulated signal in the frequency range of from, say, 1 to 10 MHz, the amplitude of which signal varies with the magnitude of the acoustical energy incident on the transducer element. Typically, the input would be obtained from a preamplifier physically located adjacent the transducer element and connecting the transducer element output to the input terminals 12 and 14. Again, the use of the system and frequency range of operation thereof is merely exemplary and is not to be construed as limiting the invention.

The illustrated amplifier means 10 includes first and second integrated circuit differential amplifiers 20 and 22 which may be of identical construction. The integrated circuit amplifiers may be of the type manufactured by Motorola, Inc., under the designation MC 135OP. Details of the amplifier circuits and the operating characteristics thereof are contained in the Motorola publication entitled *Linear Integrated Circuits Data Book* (1st ed., Dec. 1971) and are specifically incorporated herein by reference. For present purposes it will be understood that the differential amplifiers 20 and 22 each include a pair of input terminals 4 and 6, a pair of output terminals 1 and 8, a gain control terminal 5 and power supply terminals 2, 3 and 7. For both amplifiers the terminals 3 and 7 are connected to ground potential, and the terminals 2 are connected through suitable filter networks to the +10v terminal of a gated receiver power supply 24.

The gain of the amplifiers 20 and 22 is set by the d-c potential applied to the terminals 5 thereof, and in the illustrated arrangements the amplifiers 20 and 22 function as variable and fixed gain amplifiers, respectively. For this purpose the gain control terminal 5 of amplifier 20 is connected through an isolating circuit 26 to a master gain control circuit 27, whereby a manually controlled variable d-c potential may be applied to the amplifier for gain control thereof. In the logarithmic mode of operation a second component of variable gain control voltage is supplied to the gain control terminal 5 over line 30 from a signal level detector 32. With the illustrated MC 1350P-type amplifier 20, the gain control input impedance varies widely with different amplifiers and the isolating circuit 26 is used to isolate the gain control voltage sources therefrom. For amplifier 22 the gain control terminal 5 is connected to ground potential through a resistor 34 included in a voltage divider network for application of a fixed gain conrol potential thereto.

The input signal at terminals 12 and 14 is coupled through the capacitors 16 and 18 to the input terminals 4 and 6 of the differential amplifier 20, and the push-pull amplifier output from terminals 1 and 8 is developed across tuned circuits which include inductors 36 and shunt capacitors 38. The inductors 36 connect the output terminals 1 and 8 to the gated +10v power supply, and the capacitors 38 connect the same to ground potential. Capacitors 40 couple the amplifier 20 output to the input terminals 4 and 6 of amplifier 22, across which terminals resistor 41 is connected for wideband operation of the coupling network.

As noted above, the amplifier 22 operates in a constant gain mode, the gain control terminal 5 thereof being connected to resistor 34 included in a voltage dividing network connected between the gated +10v supply and ground potential. The push-pull amplifier 22 output is capacitance coupled to the signal level detector 32 by a tuned coupling network similar to that described above for the interconnection of amplifiers 20 and 22. In brief, the coupling includes tuned inductors and capacitors 42 and 44, respectively, coupling capacitors 46 and center tapped load resistor 48. The inductors 42 are connected to the gated +10v supply through RC filter means and the tuning capacitors 44 have one terminal connected to ground potential. The resistor 48 center tap is connected through RC filter means to a gated +4.6v d-c bias potential from the gated receiver power supply 24, the purpose of which biasing potential is described below. It here will be noted that the power supply 24 is gated on and off by application of a receiver gate control signal 84 at the control terminal 25 thereof for simultaneously gating on and off the + 10v and +4.6v outputs therefrom.

The signal level detector 32 to which the amplified push-pull signal from amplifier means 10 is fed comprises a full wave rectifier comprising rectifier transistors 50 and a low pass filter comprising an RC network of resistor 52 and capacitor 54 for smoothing the rectified signal. The illustrated signal level detector comprising the full wave rectifier and low pass filter commonly is termed an envelope detector since the output therefrom comprises the envelope of amplitude modulated input signals applied thereto. The transistors 50 are connected in a common collector configuration, with the emitter electrodes thereof connected together and through a load resistor 56 to ground potential and with the collector electrodes directly connected to the +10v terminal of the gated power supply 24. With no input signal supplied to the detector 32 from the amplifier means 10, the d-c bias potential at the transistor base electrodes supplied thereto from the gated power supply through resistors 47 and 48 forward biases the transistors 50, whereby the voltage developed across the load resistor 56 approximately equals the base potential of, say, +3.8v. When a push-pull signal is supplied to the detector from the amplifying means 10, the transistors 50 alternately conduct and the transistor rectifier output includes the d-c bias potential component and full wave rectified signal component. The rectified signal component is filtered by the low pass filter comprising resistor 52 and capacitor 54, and the composite rectified a-c and d-c bias signal is coupled to signal storage means 60 through receiver signal gating means 62 when the gating means is enabled. Depending upon the value of components employed, the signal level detector 32 may provide an output dependent upon peak, average, rms or other value of the signal supplied thereto.

The signal storage means simply may comprise a capacitor which is charged to the peak signal from the signal level detector 32 while the receiver signal gating means 62 is enabled. The gating means 62 includes a series gating transistor 64 through which the detected signal is coupled to the capacitor 60 when the gating means is enabled and a shunt gating transistor 66 through which the detected signal is shunted to substantially ground potential when the gating means is disabled. The shunt gate transistor 66, which is connected in a common emitter configuration, is supplied at the base electrode with a receiver gate control signal operating between, say, +5 and −2v. Transistor 66 is driven into saturation with the forward biasing positive gate control pulse applied thereto to effectively short the detector output to ground. During the negative gate control pulse, the transistor 66 is switched to a nonconducting state and the detector 32 output appears at the base electrode of series gating transistor 64 to render the same conductive. With the emitter-base junction of the series transistor 64 forward biased, there is little voltage drop across it and the signal storage capacitor 60 is charged to substantially the detector output voltage. If the detector output voltage drops below the charge on the capacitor 60, the series gating transistor 64 is cut off by the reverse emitter base junction potential, and the signal storage capacitor retains its peak signal charge. It will be seen, then, that the analog charge on the signal storage capacitor 60 is related to the maximum signal input to the system at input terminals 12 and 14 when the receiver power supply 24 is gated on, and the signal gating means simultaneously is enabled to pass the amplified and detected signal from the signal level detector 32 to said storage capacitor 60.

The analog signal stored by the capacitor 60 subsequently is coupled to a utilization means 70, such as a cathode ray tube, through readout gating means 72, which may be under control of a commutator circuit (not shown) for sequential connection of a plurality of such signal storage capacitors to the cathode ray tube for application of a composite signal thereto. Such commutator control means are shown in the above-mentioned patent application Ser. No. 411,729 and will not be repeated here. For present purposes it will be seen that the readout gating means 72 includes a field effect transistor (FET) 74 which is switched between on and off conditions by transistor switching means 76. The output from the signal storage unit 60 is applied to the FET source, and the utilization circuit 70 is connected to the FET drain. The FET gate is directly connected to the collector electrode of the switching transistor 76, and a +11v operating potential is supplied to the transistor 76 through a load resistor 78.

The switching transistor 76 normally is in saturation by reason of application of a +5v voltage to the base electrode thereof, whereby the transistor 76 collector and FET 74 gate are at substantially ground potential. As a result, the gate source junction of the FET is reverse biased by application of the positive potential signal stored on the signal storage capacitor 60. Under such conditions the capacitor 60 maintains its charge and no signal is coupled to the utilization circuit 70 therefrom. Upon application of a negative readout pulse to the switching means 72, the transistor 76 is cut off and the potential at the collector thereof and at the FET 74 gate rises toward the +11v supply voltage. The FET source gate junction thereby is forward biased for conduction of the FET for passage of the analog signal stored on capacitor 60 to the utilization circuit 70.

If the signal storage capacitor 60 is not discharged during readout, it may be discharged after readout by use of a discharge switching transistor 80 connected between the output from the FET 74 and ground potential. The FET 74 and transistor switch 80 simultaneously are rendered conductive by application of a negative discharge pulse to the base of transistor 76 in the readout gating means 72 and a positive discharge pulse to the base electrode of discharge switching transistor 80, for connection of the capacitor 60 to substantially ground potential through the now conducting FET 74 and transistor 80. When the signal storage device has been discharged at the completion of the discharge pulse, the circuit is in condition for another cycle of operation.

Figure 2:
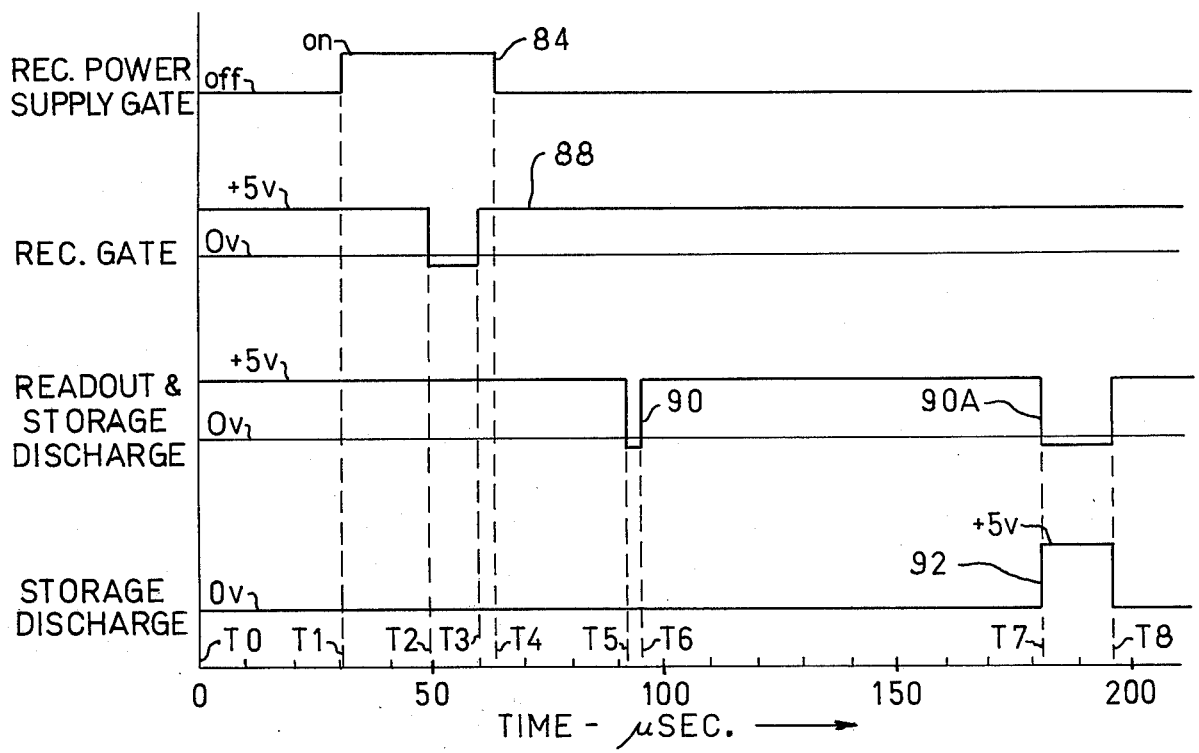
FIG. 2 is a diagram of waveforms useful in explaining the operation of the system shown in FIG. 1.

A brief description of the operation of the system shown in FIG. 1 now will be made with reference to the waveform diagram of FIG. 2. At time T0 the signal storage capacitor 60 is discharged and the power supply 24 is off. The power supply is gated on at time T1 by receiver power supply gate pulse 84 for supply of the +10v and +4.6v operating and bias potentials to the system. While the receiver operation stabilizes, no output from the signal level detector 32 to the signal storage device 60 is provided, since the +5v receiver signal gate control voltage 88 switches on the shunt gating transistor 66 to substantially short circuit the signal level detector output to ground potential. When the receiver operation has stabilized, the receiver signal gate control pulse 88 goes negative between times T2 and T3 to cut off shunt transistor 66, whereupon the signal level detector 32 output is supplied to the signal storage capacitor 60 through the series gate transistor 64. The capacitor 60 is charged to the highest, or peak, level of the voltage appearing at capacitor 60 during this time and holds the charge after the receiver signal gate control voltage 88 returns to +5v at time T3.

Following termination of the receiver gating pulse, or substantially simultaneously therewith, the power supply 24 is gated off by the end of power supply gate pulse 84 to remove power from the illustrated amplifier and signal level detector and all other such amplifiers and signal level detectors (not shown but which would be included in an arrangement such as the acoustic camera shown in patent application Ser. No. 411,729). By removing receiver power during much of the operating cycle, temperature stablization is more readily accomplished and power dissipation is reduced. Even with the power supply gated off, the charge on the signal storage capacitor 60 is maintained at the peak level since the storage device is isolated at both its input and output by the nonconducting series gating transistor 64 and FET 74, respectively.

At time T5 a negative readout pulse 90 is applied to the readout gating means 72 to cut off transistor 76 and thereby switch on the FET 74. The potential charge on the storage device 60 thereby appears at the input to the utilization device 70 during the presence of the readout pulse, T5 to T6. Subsequently, at time T7 the storage capacitor 60 is discharged to ground potential by simultaneous application of a negative discharge pulse 90A at the readout means 72 to switch on the FET 74 and a positive discharge pulse 92 to the transistor 80 to shunt the off from the FET to ground potential thereof and the now conducting transistor 80. At time T8 the discharge pulse 92 is terminated and the circuit is in condition for another cycle of operation.

The gain control circuits for the amplifier means 10 and the means for switching between linear and logarithmic modes of amplifier operation now will be described. As seen in FIG. 1, a master gain control potentiometer 28, across which the gated +10v supply is connected, is used for manually setting the zero input signal gain of the illustrated amplifier means 10 and the gain of every other such amplifier means which may be included in the system. For example, in patent application Ser. No. 411,729 the master gain control is used for simultaneously manually setting the gain of 192 similar amplifier means in an acoustic camera system. The master gain control obtained from the movable arm of the potentiometer 28 is connected through low pass filter means to the junction between resistors 100 and 102, which comprise a voltage divider network connected between the gated supply for amplifiers 20 and 22 and common ground potential. This junction, in turn, is connected through the isolating network 26 to the gain control terminal 5 of the amplifier 20 to control the gain thereof. All of the amplifier means in the system are provided with individual gain control potentiometers 98, which also are connected between the gated supply for amplifiers 20 and 22 and ground potential. The movable arm of the potentiometer 98 also is connected through low pass filter means to the junction between the voltage divider resistors 100 and 102. The potentiometers 98 function as individual trimmer controls for balancing the gains of all such amplifier means which may be included in the system. A third variable component of gain control voltage may be supplied to the junction between resistors 100 and 102 over line 30 from the signal lever detector 32 output in a manner described below.

Different integrated circuit amplifiers 20 have widely varying low impedances at the input to the gain control circuits thereof. The isolating network 26 is included to minimize the effects of such impedance variations on the gain control voltage source, thereby minimizing differences in amplifier operations. The isolating network may simply comprise a transistor 96 connected in an emitter follower configuration to which the gain control voltage at the junction of resistors 100 and 102 is connected. The load resistor 106 is connected to the gain control terminal 5 of the amplifier 20 through a diode connected transistor 104. The interconnected base and collector electrodes of the diode connected transistor 104 are connected through a resistor 107 to the gated supply for amplifier 20 to forward bias the same. With this arrangement the widely varying load provided by the amplifier 20 gain control circuit is sufficiently isolated from the input to the network 26 to have a negligible effect on the input impedance thereof.

With the gain control terminal 5 of amplifier 20 at some fixed value as set by the gain control potentiometers 28 and 98, the amplifier means 10 operates in a substantially linear mode, such that the output therefrom is substantially directly linearly related to the input signal at terminals 12 and 14. For logarithmic operation, the output from the signal level detector 32 is supplied over line 30 as a variable gain control component to the amplifier 20. A transistor switch 108, when rendered conductive by application of a positive control voltage at the base electrode thereof, serves to connect the signal level detector 32 output to the gain control circuit.

Figure 3:
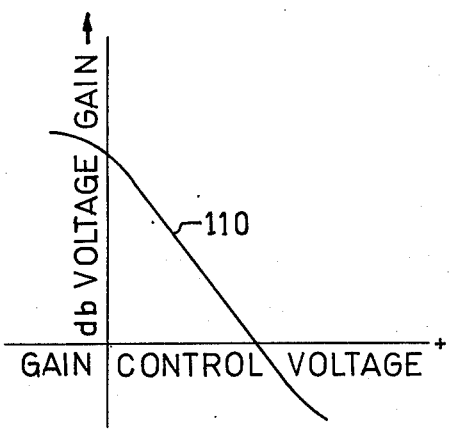
FIG. 3 is a graph showing db voltage gain versus gain control potential for an amplifier included in the system of FIG. 1.
Figure 4:
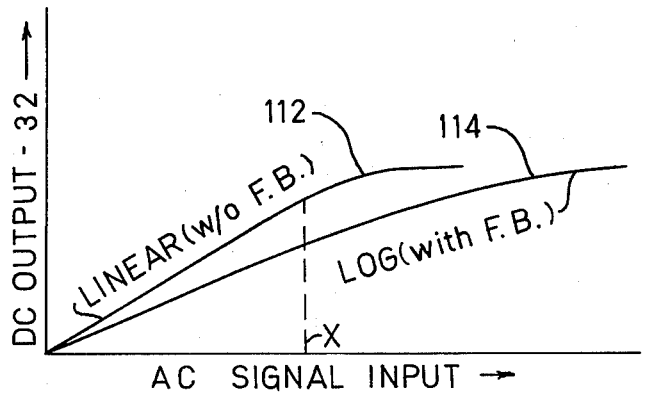
FIG. 4 is a graph showing the d-c signal level detector output versus a-c signal input for both linear and logarithmic modes of amplifier operation.

Reference is made to FIG. 3 wherein a graph 110 of the db voltage gain for amplifier 20 versus gain control voltage at terminal 5 shows that the changes in db voltage gain are linear over a wide range of gain control voltage. In FIG. 4 the d-c output from the signal level detector versus a-c signal input to the amplifier means for both linear and logarithmic operations is shown. With no feedback to the gain control circuit, i.e., with switching transistor 108 turned off, and at some fixed level of gain as provided by the manually operated potentiometers 28 and 98, the output from the signal level detector 32 varies substantially linearly with changes in the a-c signal input up to an input level designated X, at which point nonlinearity operation begins. With gain control feedback, i.e., with the switching transistor 108 in the conducting state, the d-c output from the signal level detector 32 is seen to vary logarithmically with changes in a-c signal input. It will further be noted that the logarithmic operating mode not only covers the same range as the linear operating mode, but extends beyond the a-c input signal level X at which distortion occurs in the linear mode of operation. It is seen, then, that operation over a wider range of input signals is possible in the logarithmic mode than in the linear mode.

With the power supply gated on and the signal gating means 62 conditioned to pass the output from the signal level detector 32 to the storage device, it will be apparent that the output from the detector with no a-c input to the amplifier means depends solely upon the d-c bias potential supplied by the +4.6v terminal of the gated receiver power supply. In accordance with a feature of the invention, this +d-c bias potential is selected to provide the signal level detector 32 with an output component due to said d-c bias which substantially equals the gain control voltage at the line 30 with the manually operated gain control potentiometers 28 and 98 set at substantially normal operating levels for the linear operating mode. For example, if in the linear operating mode a +3.5v gain control potential is applied to line 30 to provide the desired level of output signal to the utilization device under nominal operating conditions, then the gated d-c bias potential would be selected to provide substantially a +3.5v output from the signal level detector with zero a-c signal input. Consequently, with no input signal to the amplifier means, the emitter collector voltage for the linear-logarithmic switching transistor 108 is substantially zero. As a result, the transistor 108 may be switched between conducting (logarithmic) and nonconducting (linear) conditions without changing the level detector 32 output under no a-c input signal conditions to the amplifier. Any need to readjust the master gain control potentiometer 28 each time the receiver 10 is switched between logarithmic and linear modes of operation thereby is avoided.

The invention having been described in detail in accordance with the requirements of the Patent Statutes, various changes and modifications will suggest themselves to those skilled in this art. It will be apparent that other amplifiers than the integrated circuit amplifiers type MC 1350P may be used. Also, operation with either conventional logarithmic or linear amplifiers without switching between the two modes of operation is contemplated. If no switching is employed, the application of the d-c bias to the detector 32 is not required and can be eliminated. Also, the amplifier which operates in either a logarithmic or linear mode, as illustrated, may be employed without the subsequent signal switching, storing and readout means, and without gating of the power supply, if desired. In addition, a digital memory using, for example, semiconductor means may be employed as the signal storage means 60 in place of the illustrated capacitor. It is intended that these and other such modifications and changes which fall within the spirit and scope of the invention will be covered by the appended claims.

What is claimed is:

1. In a system for use in processing an amplitude modulated carrier signal such as a signal produced by an ultrasonic transducer element, or the like, included in an array of such elements:
   amplifier means having an output and an input to which an amplitude modulated carrier signal is connected;
   an envelope detector comprising rectifier and low pass filter means connected to the amplifier means output;
   signal storage means;
   signal gating means operable between enabled and disabled conditions for connecting the output from said envelope detector to said signal storage means when enabled; said signal gating means being recurrently enabled for time periods which extend over a plurality of cycles of said carrier signal;
   said signal storage means consisting of a capacitor which is charged according to the magnitude of the output from said envelope detector during the enabled condition of said signal gating means;
   means including readout gating means connected to said capacitor for connecting said capacitor to a utilization circuit when said signal gating means is disabled;
   means for enabling said readout gating means for a time during which said signal gating means is disabled to provide an output from said readout gating means which is directly related to the amplitude of the signal stored by said capacitor;
   discharge switching means connected between the output from the readout gating means and ground potential; and
   means for simultaneously enabling said readout gating means and discharge switching means for connecting the output from the capacitor to ground potential.

2. In the system of claim 1 including:
   a gated power supply for supplying power to said amplifier means and envelope detector; and
   means for gating off said power supply during at least a portion of the time that said signal gating means is disabled.

3. A circuit for logarithmic amplification of an amplitude modulated carrier type input signal comprising:
variable gain amplifier means having at least one output, a gain control terminal and at least one input to which an input signal is supplied, the db voltage gain of said amplifier means varying substantially linearly over a range of voltages applied to said gain control terminal;
a signal envelope detector having an input and an output and providing a variable d-c voltage at the output thereof which is proportional to the level of signal applied to the input thereof;
means for applying the output from said amplifier means to the input of said signal envelope detector; and
means for connecting the output from said signal envelope detector to said gain control terminal of said amplifier means for varying the gain of said amplifier means whereby said amplifier output varies substantially logarithmically with changes in input signal thereto.

4. The invention as defined in claim 3, wherein said means for connecting the output from said signal envelope detector to said gain control terminal includes switching means for opening and closing said connecting means for switching between linear and logarithmic operation of said amplifier means.

5. The invention as defined in claim 4, wherein said switching means comprises a transistor operable between cutoff and conducting conditions.

6. The invention as defined in claim 4 including:
a manually controlled gain control source also connected to said gain control terminal; and
a d-c bias supply connected through said signal envelope detector to said switching means for establishing a substantially zero potential drop across said switching means, with zero input signal to said amplifier means in the cutoff condition of said switching means.

7. The invention as defined in claim 4, wherein the level of gain control signal to said gain control terminal is substantially the same in both switch open and switch closed conditions, with zero input signal to said amplifier means.

8. The invention as defined in claim 3 including:
signal storage means; and
means for alternately connecting and disconnecting said signal envelope detector output signal to said signal storage means.

9. The invention as defined in claim 8, wherein said means for alternately connecting and disconnecting said signal envelope detector output signal to said signal storage means comprises a combination shunt and series gating circuit for alternately shunting the output signal from said signal envelope detector to ground potential and connecting said output signal to said signal storage means.

10. The invention as defined in claim 8 including:
a gated power supply for supplying power to said amplifier means; and
means for gating off said power supply during at least a portion of the time that said signal envelope detector output signal is disconnected from said signal storage means.

11. A method for providing logarithmic amplification of an amplitude modulated carrier type input signal comprising:
applying an amplitude modulated carrier input signal to a variable gain amplifier means having a db voltage gain characteristic which varies substantially linearly over a range of voltages applied to a gain control terminal of the amplifier means;
envelope detecting the amplified signal output from said amplifier means; and
applying the envelope detected signal output to the gain control terminal of said amplifier means to vary the gain of the amplifier means whereby the amplified output signal varies substantially logarithmically with changes in input signal thereto.

12. The method as defined in claim 11 which includes connecting the envelope detected signal output to the gain control terminal of said amplifier means through a switching means operable between open and closed conditions for selectively switching between linear and logarithmic operation of said amplifier means.

13. The method as defined in claim 12 including supplying a d-c bias to said switching means through envelope detecting means to establish a substantially zero potential drop across said switching means with zero input signal to said amplifier means in the cut off condition of the switching means.

* * * * *